United States Patent
Usenius et al.

[11] Patent Number: 5,887,588
[45] Date of Patent: Mar. 30, 1999

[54] AUTOMATED METHOD FOR CLASSIFICATION AND QUANTIFICATION OF HUMAN BRAIN METABOLISM

[76] Inventors: Jussi-Pekka R. Usenius, Isolanti, Fin-40950 Muurame, Finland; Risto A. Kauppinen, Presidentinkatu 40, FIN 70620 Kuopio, Finland; Sakari Touhimetsa, Vilpunlaakso 29, FIN-92130 Raahe, Finland; Yrjo Hiltunen, Parkumaentie 5, FIN-90860 Halosenniemi, Finland; Pamli Vainio, Julkulanniementie 2S, FIN-70100 Kuopio, Finland; Mika J. Ala-Korpela, Tilkkaajantie 18, 96910 Rovaniemi, Finland

[21] Appl. No.: 394,341
[22] Filed: Feb. 23, 1995
[51] Int. Cl.$^6$ .................................................. A61B 5/055
[52] U.S. Cl. ......................... 128/653.2; 395/21; 395/924
[58] Field of Search ................................ 128/653.2, 920, 128/923; 364/413.02; 395/924, 20, 21

[56] References Cited

U.S. PATENT DOCUMENTS

| | | | |
|---|---|---|---|
| 5,218,529 | 6/1993 | Meyer et al. ........................ | 364/413.01 |
| 5,283,526 | 2/1994 | Spielman et al. ..................... | 128/653.2 |
| 5,490,516 | 2/1996 | Hutson ................................. | 128/696 |

OTHER PUBLICATIONS

Cross et al., "Introduction to neural networks", *The Lancet*, vol. 346, Oct. 21, 1995, pp. 1075–1079.

William G. Baxt, "Application of artificial neural networks to clinical medicine", *The Lancet*, vol. 346, Oct. 28, 1995, pp. 1135–1138.

Usenius et al., "Automated classification of human brain tumours in neural network analysis using in vivo $^1$H magnetic resonance spectroscopic metabolite phenotypes", *NeuroReport*, vol. 7, No. 10, Jul. 1996, pp. 1597–1600.

*Primary Examiner*—Ruth S. Smith
*Attorney, Agent, or Firm*—Cushman, Darby & Cushman; IP Group of Pillsbury, Madison & Sutro LLP

[57] ABSTRACT

A method for analyzing human brain physiology and pathology according to metabolic data obtained by non-invasive means. Metabolism is detected using in vivo proton nuclear magnetic resonance spectroscopy ($^1$H MRS) using pulse sequences that provide nuclear magnetic resonance signals from a living human brain. Factors which might decrease performance of artificial neuronal network analysis, e.g. the residual water signal, are eliminated from the nuclear magnetic resonance signal, e.g., by means of a singular value decomposition algorithm. Moreover, the artificial neuronal network analysis accepts as input all of the metabolite resonances, not just selected features, for analysis. The artificial neuronal network analysis yields metabolite concentrations and the nature of tissue type in focal lesions, such as tumors, stroke lesions, epileptic foci, traumatic scars, and also in more diffuse pathologies such as metabolic brain disorders as well as in post-therapeutic changes. The method can provide automated classification procedure of human brain tissue histology for clinical use.

3 Claims, 3 Drawing Sheets

AUTOMATED METHOD FOR CLASSIFICATION AND QUANTIFICATION OF HUMAN BRAIN METABOLISM

FIELD OF INVENTION

The present method utilizes human brain metabolite patterns, obtained non-invasively by means of nuclear magnetic resonance spectroscopy, in classification of focal and global disorders.

BACKGROUND OF THE RELATED ART

Specific diagnosis of a number of human brain disorders demands extensive use of a number of imaging methods, such as computer assisted tomography (CT) and nuclear magnetic resonance imaging (MRI), recording of spontaneous and evoked electrical activity, but very often also open craniotomy to obtain a specimen from the tissue for microscopic examination. While the imaging methods and extracranial electrical recordings are non-invasive, in other words contain neither immediate patient management nor health risk, open cranial biopsies or electrical recordings intracranially pose given risks for the subjects. Both CT and MRI are capable of imaging anatomy in great detail, but they do not provide information from the type of pathology in question. Consequently, their value in neuroradiological diagnosis currently is twofold; firstly, to locate the pathology and secondly, to guide neurosurgeons in determining the site for the open biopsy procedure.

It is technically possible to record non-invasively metabolic information by water-suppressed proton nuclear magnetic resonance spectroscopy ($^1$H MRS) with high degree of volume-selection from human brain regions. This method has made it possible to approach brain metabolism both in healthy and diseased human subjects without immediate harms. Brain metabolites that can be visualised by $^1$H MRS, provides different type of information than either CT or MRI do. CT indicates absorption of X-rays in the brain tissue and MRI probes magnetic properties of water molecules and sometimes also those of fat. $^1$H MRS reveals specific biochemical compounds which reflect metabolic activity of both normal and abnormal brain. These include N-acetyl aspartate, creatine+phosphocreatine, choline-containing compounds, myo-inositol, scyllo inositol, glutamic acid, glutamine, lactic acid, adenine nucleotides as well as portions of mobile fat and protein moieties.

The conventional in vivo $^1$H MRS data processing is accomplished by means of peak integration or peak fitting of signals from the assigned metabolites. This type of data analysis, however, is prone to several technical flaws which are user-biased and therefore both biochemically and diagnostically useful information may become overruled. Also $^1$H MRS artefacts, such as prominent residual water signal have made previous efforts of metabolic classification according to the spectral information ambiguous. Metabolite quantification by ANN relys on simulated or empirically measured reference material and the test sample is compared with the former data set. Therefore the metabolite quantification procedure is independent of many technical difficulties such as signal intensity quantification and determination of relaxation parameters.

SUMMARY OF THE INVENTION

The aim of this invention is to utilize human brain metabolite patterns that are detected non-invasively, in an automated classification of histological or pathological nature of tissue. Furthermore the aim of this invention is to bring orward a method, which will reveal the metabolite phenotypes in given pathologies into a clinical context.

The aim of the invention is accomplished by the method characterized in the appended claims.

An automated method for analysis of human brain metabolism is described. Metabolism is detected by means of proton nuclear magnetic resonance spectroscopy using pulse sequences that yield nuclear magnetic resonance signals from human brain. Nuclear magnetic resonance signal is processed in a manner eliminating factors that might decrease performance of the artificial neural network analysis. The processed signal is analysed in an artificial neuronal network which yields as results biochemical patterns in the human brain tissue.

According to the invention the automated method can be applied to determine diagnoses of neural tissue both in focal lesions or in disorders with anatomically normal-appearing brain as detected by MRI. MRI will not directly give definitive indications of the nature of such lesions which could include tumors, infarcts, cysts, scars, and post-therapeutic effects. This method also indicates nature of brain tissue in cases where MRI does not depict abnormality such as in epileptic foci or global metabolic disorders.

In the present method an effective postprocessing technique is utilised to remove residual water signal from in vivo $^1$H MRS data and an ANN analysis of spectral patterns in classification of brain lesions. This type of automated handling of in vivo $^1$H MRS data is user-independent and simple for clinical purposes. Also the whole $^1$H MRS information is taken into account in classification procedure by ANN analysis. The method yields brain tissue classification according to clinically useful way in a number disorders such as tumors, epileptic foci, stroke lesions and many of the metabolic brain disorders. The method could markedly reduce the need for surgical biopsies prior to diagnosis.

The method bases on the ability of trained fully-conducted ANN to group brain metabolite patterns (from $^1$H MRS recorded from the human brain) according to the nature of tissue within the volume of interest. Instead of fully-conducted ANN or together with it, a self-organizing ANN can be used for formation of output-classes. It should be emphasised that the classification of human brain tissue by ANN does not relay on simple biochemical factor in the given volume of interest. This method can also be used for determination of in vivo concentrations of the metabolites within the volume of interest. This happens by training the ANN with computer-simulated or empirically measured quantitative metabolite data.

BRIEF EXPLANATION OF THE ILLUSTRATIONS

FIG. 1. shows a schematic representation of the components required for the $^1$H MRS data collection and processing from signal detection to determination of diagnosis.

FIG. 2. illustrates a set of $^1$H MRS spectra of ANN training set recorded from specified brain tissue types as follows:

FIG. 2A, normal brain tissue;

FIG. 2B, astrocytoma grade 2;

FIG. 2C, glioblastoma;

FIG. 2D, meningeoma.

FIG. 3. shows the arbitrary weightfactors from ANN as a function of resonance frequency.

DESCRIPTION OF PREFERRED EMBODIMENTS

Figure 1:
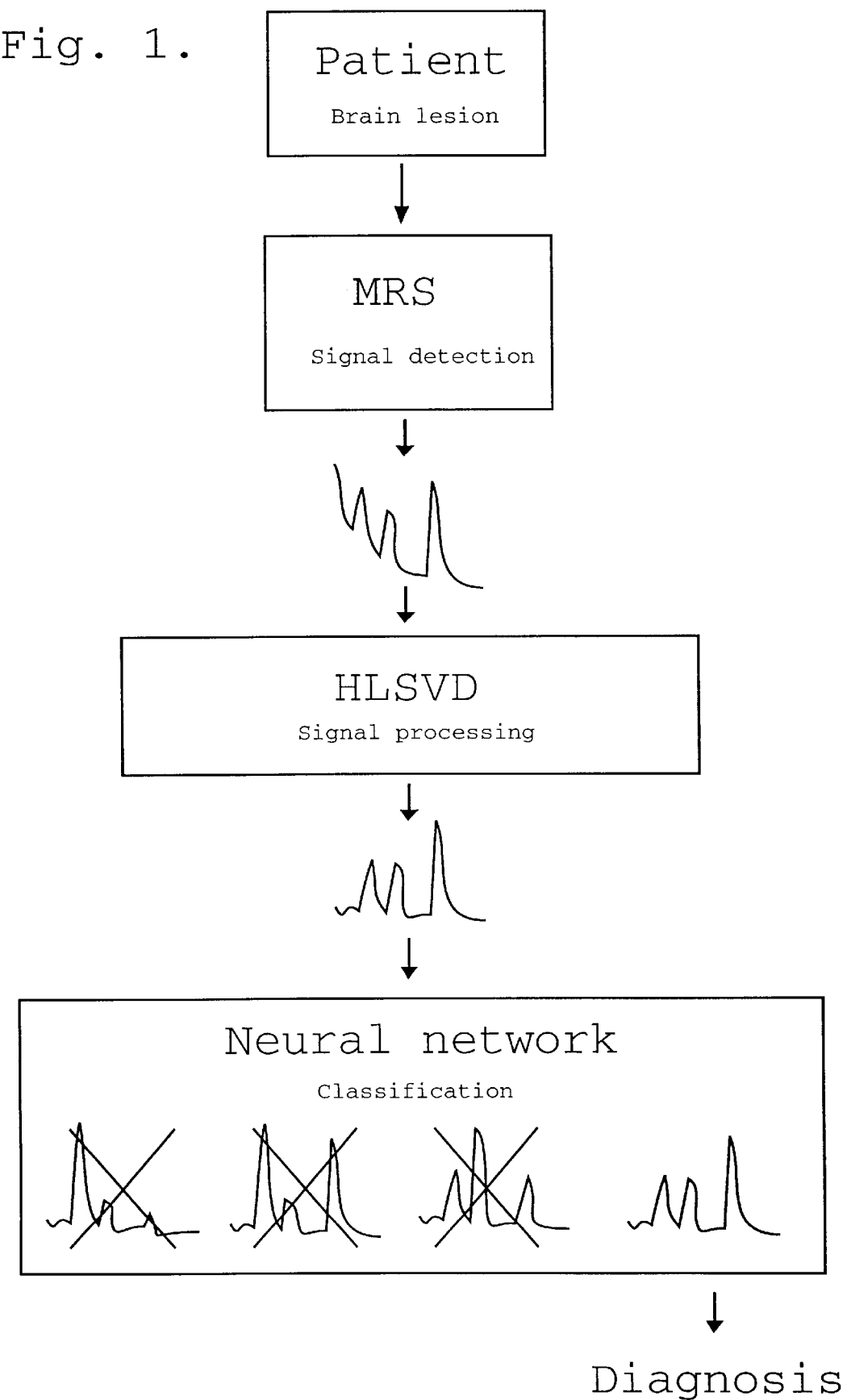

The entire invention is schematically represented in FIG. 1. A patient is positioned in the MRS scanner and MR-imaging scans are acquired to determine the volume of interest. The volume of brain from which $^1$H MRS spectra are collected is determined, as required in each case separately.

The MRS signal is processed so that signals disturbing assessment of metabolite signals, are eliminated. The resulting MRS data, which can be in either time domain or frequency domain format, are analysed by means of artificial neural network (ANN). This neural network is trained by the $^1$H MRS data of human brain metabolites in a manner so that it classifies metabolite phenotypes according to the nature of the tissue in the volume of interest. ANN output can be thus either a clinical diagnosis or a concentration of given metabolite. It is expected that a self-organising neural network can be used prior to a fully-connected ANN or even instead of it.

In the following we will describe an application of this method. These results demonstrate the classification power of the method in the case of human brain tumors.

The single voxel double-spin echo PRESS sequence (sweepwidth of 1000 Hz, 1024 complex data points, echo time of 270 ms, repetition time of 1500 ms, 256 scans) was used for data acquisitions of in vivo $^1$H MRS in a Siemens Magnetom SP63 scanner operating at 1.5 T with a routine quadrature, circularly polarised head coil. Volume of interest was 8 ml (2 cm a square), and its localization was controlled by means of a $T_2$-weighted multisection FLASH images (510/18/15°). Water suppression was accomplished by three Gaussian-shaped CHESS pulses with bandwidths of 60 Hz. Eight scans were acquired without water suppression to determine tissue water signal intensity and to obtain a data set for residual eddy currents compensation.

Thirty two patients with thirteen different histological types or grades of brain tumors (gliosis, astrocytoma of grades from 1 to 3, glioblastoma multiforme, oligodendroglioma of grades 1 or 2, neurilemmoma, benign and atypic meningeoma, pituitary adenoma, neuroblastoma and metastasis of melanoma, see Table 1) were included in the tumor data set. Tumors were located either in cerebrum or cerebellum and the diameter of solid part of the tumor was 2 cm or greater in diameter so that signal contamination from cysts or normal brain tissue was minimal. The control material comprised of healthy contralateral parietal lobes of six patients and ten volumes recorded from five brain regions of ten healthy volunteers (two volumes from frontal, parietal, occipital, temporal and thalamic areas, respectively).

First data processing step comprised of removal of residual water signal. The echoes were corrected for eddy current induced phase modulation. The corrected echoes with 1024 data points were zero filled to 2048 points. Before Fast Fourier Transformation and manual zero order phase correction residual water signal in the data set was removed using the Hankel Lanczos Singular Value Decomposition (HLSVD)-method. One to eight components within the water chemical shift region were subtracted from the original echo leading to the reduced echo free from water resonances, a procedure that does not affect metabolite resonances outside the water region. Water signal intensity of the non-suppressed volumes was calculated with the same HLSVD program using an IBM compatible PC and it was used as a reference for the metabolite data.

TABLE 1

Histological types and classes of brain tumors and numbers in training and test sets.

| Diagnosis | Predicted class [a] | Number of samples in training set | Number of samples in test set |
|---|---|---|---|
| gliosis | BG | 1 | |
| astrocytoma grade 1 | BG | 2 | |
| astrocytoma grade 2 | BG | 4 | 3 |
| astrocytoma grade 3 | MG | 2 | |
| glioblastoma | MG | 5 | 2 |
| oligodendroglioma grade 1 | BG | 1 | |
| oligodendroglioma grade 2 | BG | 2 | |
| neuroblastoma | O | 1 | |
| neurilemmoma | O | 1 | |
| pituitary adenoma | O | 2 | |
| benign meningeoma | O | 2 | 2 |
| atypic meningeoma | O | | 1 |
| melanoma metastasis | O | 1 | |
| contralateral normal | C | 4 | 2 |
| volunteer normal | C | 8 | 2 |

[a] Class: benign glioma, BG; malignant glioma, MG; other tumor, O; control, C

Second data processing step comprised of artificial neural network analysis. A filly connected multilayer neural network was used with either 308 or 309 input neurons, 9 hidden neurons and 4 output neurons. The back-propagation algorithm was used in the training procedure. An IBM compatible 486-66 Mhz PC was used for both programming and software management. The approximated training time of the networks were 0.5 to 1 hours including 1000–2000 iteration cycles. The classifications using trained ANNs are instant.

Figure 2A:
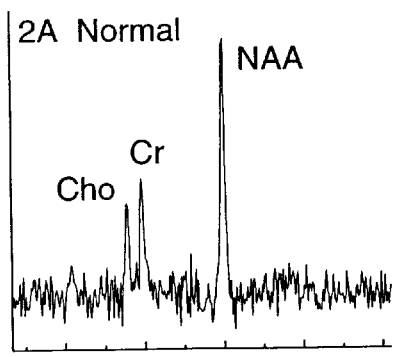
Figure 2B:
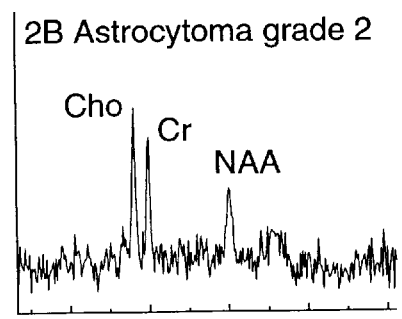
Figure 2C:
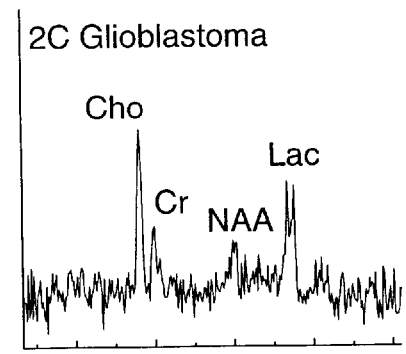
Figure 2D:
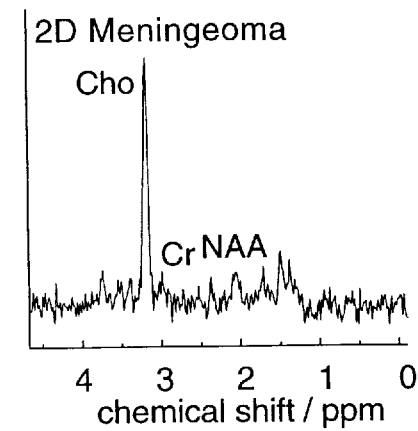

Two different in vivo $^1$H MRS data sets were used as an input to the ANNs: either the 308 spectral points (from 4.2 to −0.5 ppm) in the metabolite spectra were used as such or they were referenced to the unsuppressed water signal in the same volume with an additional input formed by dividing the spectral area by the unsuppressed water resonance area in the same volume. These data sets provided simple metabolite patterns and water-referenced relative concentrations of these compounds, respectively. All the inputs were scaled between 0 and 1. The training group included 36 cases and the test group 12 cases as specified in Table 1. Table 1 summarizes the whole training and test sets of 48 cases. Based on the clinically relevant issues, the ANN outputs were coded in benign glioma, malignant glioma, other type of tumor or normal. A set of typical spectra from four main diagnoses (normal, astrocytoma of grade 2, glioblastoma and meningeoma) are shown in FIG. 2A. to FIG. 2D. respectively.

Using the metabolite phenotypes, all the tumors were separated from the healthy brain by ANN (Table 2). Classification of brain tissue into four clinically useful "histological" types (Table 1), based on metabolites with water-reference $^1$H MRS data as inputs, resulted in selection of all the malignant gliomas into their category (Table 2). Only one astrocytoma of grade 2 was incorrectly placed among "other tumors". Using metabolite data set alone, nine out of twelve tumors were correctly grouped into these four categories. One benign meningeoma and two benign astrocytomas were positioned into the group of "malignant gliomas".

Figure 3:
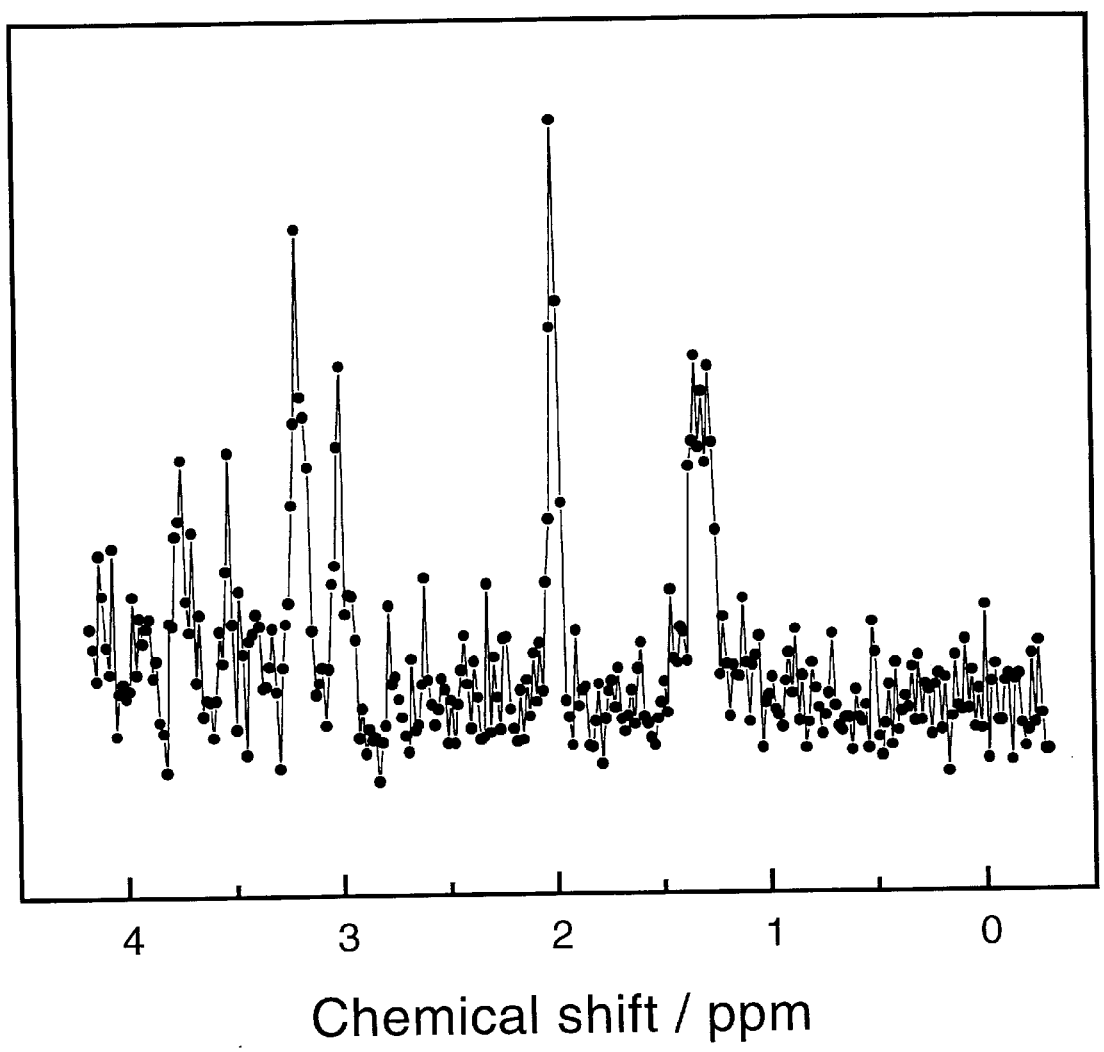

FIG. 3. shows the arbitrary weights for spectral input data points of the ANN. This "spectrum" is formed by averaging the absolute weightfactors of each frequency point of the $^1$H MRS data at the first layer of the neural network. It demonstrates the most significant points in the MRS metabolite profiles for the classification. These points clearly are associated with choline-containing compounds (Cho) at 3.2 ppm, creatine (Cr) at 3.0 ppm, NAA at 2.0 ppm and the lactate region at 1.3 ppm.

TABLE 2

Neural network classification of test set based on $^1$H MRS water related metabolite information.

| Histological type | Predicted class [a] | Output class [a] | Output value |
|---|---|---|---|
| astrocytoma grade 2 | BG | BG | 0.981 |
| astrocytoma grade 2 | BG | BG | 0.992 |
| astrocytoma grade 2 | BG | O | 0.990 |
| glioblastoma | MG | MG | 0.996 |
| glioblastoma | MG | MG | 0.952 |
| benign meningeoma | O | O | 0.924 |
| benign meningeoma | O | O | 0.999 |
| atypic meningeoma | O | O | 0.995 |
| contralateral normal | C | C | 0.999 |
| contralateral normal | C | C | 0.999 |
| volunteer normal | C | C | 0.999 |
| volunteer normal | C | C | 0.999 |

[a] Class : benign glioma, BG; malignant glioma, MG; other tumor, O; control, C

The present results show that an automated, user-independent treatment of spectroscopic neuroimaging data using ANN could predict histological types of brain tumors with high accuracy. This method would be expected to initiate a novel application of spectroscopic data so that no human involvement is necessary prior to prediagnostic interpretation.

The power of neural networks lies in that they can take whole spectral information into account in the analysis procedure. This feature distinguish ANN analysis from the conventional spectral analysis where only the assigned resonances are analysed either by peak-to-peak integration or by lineshape fitting. For instance, classification of brain tumors according to their metabolite $^1$H MRS data by ANN are expected to be successful even if there are no statistically significant metabolite concentration changes within the histologically distinct tumor groups. This is particularly so with respect to Cho and Cr for instance, among gliomas. Neural network can indicate, however, the given biochemical factor that it has used in the formation of groups (FIG. 3). Removal of residual water signal from the metabolite MRS data has certain evident advantages in this context. Usually, water signal causes both baseline distortion and overlap with some metabolite signals. If the time domain is not ideal, for example if there is truncation of the first data points, it will result after Fourier transform, in baseline oscillation and peak distortion over the whole spectral width.

The trained network emphasised these frequencies in its decision making (see FIG. 3). It is obvious that relaxation parameters T1 and T2 as such would provide additional information to be used as a training input to the network, which can be utilised as a means of obtaining quantitative MRS data. This kind of data set provides possibility to quantify specified metabolite concentrations noninvasively from individual brain lesions.

What is claimed is:

1. An automated method for a non-invasive analysis of human brain tissue metabolism in a brain of a living human being, comprising:

detecting metabolism of said human brain tissue using proton nuclear magnetic resonance spectroscopy with such pulse sequences to yield nuclear magnetic resonance signals from said human brain tissue;

processing said nuclear magnetic resonance signals by eliminating factors that might decrease performance of an artificial neural network analysis, including:
   removing residual water signals from said nuclear magnetic resonance signals using a singular value decomposition algorithm; and
   inputting all resulting metabolite resonances to an artificial neural network;

analyzing said input metabolite resonances with said artificial neural network to yield as a result a biochemical pattern in said human brain tissue.

2. An automated method according to claim 1, further comprising:

classifying said human brain tissue according to proton nuclear magnetic resonance spectral metabolite patterns.

3. An automated method according to claim 1, further comprising:

quantifying metabolite concentrations in selected regions of said brain of said living human being.

* * * * *